United States Patent [19]
Murray

[11] Patent Number: 5,411,052
[45] Date of Patent: May 2, 1995

[54] LIQUID SUPPLY APPARATUS

[75] Inventor: Charles G. Murray, Auckland, New Zealand

[73] Assignee: Fisher & Paykel Limited, Auckland, New Zealand

[21] Appl. No.: 47,792

[22] Filed: Apr. 15, 1993

[30] Foreign Application Priority Data

Apr. 15, 1992 [NZ] New Zealand .................. 242372

[51] Int. Cl.$^6$ .................. A61M 5/172; F16K 31/02
[52] U.S. Cl. .................. 137/392; 73/861.41; 137/487.5; 250/574; 250/576; 250/577; 604/253
[58] Field of Search .................. 73/861.41, 290 R; 137/1, 2, 386, 392, 486, 487.5; 250/573, 574, 576, 577; 604/246, 253

[56] References Cited

U.S. PATENT DOCUMENTS

| | | | |
|---|---|---|---|
| Re. 32,294 | 11/1986 | Knute | 604/253 |
| 3,563,090 | 2/1971 | Deltour | 604/253 |
| 3,890,968 | 6/1975 | Pierce et al. | 604/253 |
| 4,261,388 | 4/1981 | Shelton | 604/253 |
| 4,474,206 | 10/1984 | Cannon | 604/253 |
| 4,509,943 | 4/1985 | Hanzawa | 73/861.41 |
| 4,635,281 | 1/1987 | Jones | 604/253 |
| 4,708,831 | 11/1987 | Elsworth et al. | 604/253 |
| 4,718,896 | 1/1988 | Arndt et al. | 73/861.41 |
| 4,820,281 | 4/1989 | Lawler | 604/253 |
| 4,827,766 | 5/1989 | Nelson | 73/861.41 |

*Primary Examiner*—George L. Walton
*Attorney, Agent, or Firm*—Trexler, Bushnell, Giangiorgi & Blackstone, Ltd.

[57] ABSTRACT

Liquid supply apparatus is disclosed for controlling the supply of liquid to humidifier apparatus. The liquid supply apparatus has a chamber with an inlet through which a liquid such as water is supplied to the chamber. The chamber has a flow detector to detect liquid entering the chamber and a level detector near the base of the chamber in a narrow portion of the chamber which, in conjunction with a calibrated orifice at the chamber outlet, provides an indication of the rate of liquid flow from the chamber. Control of supply of liquid is performed by a magnetically activated valve member.

24 Claims, 4 Drawing Sheets

LIQUID SUPPLY APPARATUS

BACKGROUND OF THE INVENTION (1.) Field of the Invention

This invention relates to methods of and/or apparatus for controlling the supply of a liquid and has been particularly devised for controlling the supply of water for use in humidifying apparatus.

(2.) Description of the Prior Art

Previously, apparatus for controlling the supply of a liquid such as water to humidifying apparatus has used detectors and valves such as those disclosed in the specification of our U.S. Pat. No. 4,708,831. In that specification, a flow control device is disclosed wherein a liquid is allowed to enter a chamber in discrete drops, each drop interrupting a beam of infrared light so that the admission of each drop to the chamber is recorded by a controller. A valve comprising a spherical metallic member located on the outlet is opened by the controller when water is required to be supplied to the humidifier apparatus.

The device disclosed in U.S. Pat. No. 4,708,831 has a number of disadvantages.

Firstly, the infrared emitter and detector provide radiation across only a narrow part of the cross-section of the chamber. Therefore, if the device is mounted on an angle, rather than being mounted exactly vertically, drips of liquid entering the chamber may not interfere with the infrared radiation and not be detected.

Secondly, an indication of the flow rate, or maximum flow rate of liquid through the chamber is not provided.

Thirdly, there is no way of measuring or providing an indication of the amount of liquid which is actually in the chamber.

Fourthly, the metallic ball which acts as the valve member at the base of the chamber requires a relatively large amount of energy to move it in order to allow liquid to exit the chamber. Also, a large solenoid is required to provide the necessary magnetic flux density to move the ball.

Fifthly, the device disclosed in U.S. Pat. No. 4,708,831 does not have a non-return valve to prevent liquid flowing back into the chamber when the magnetic ball valve is opened.

It is an object of the present invention to provide methods of and/or apparatus for controlling the supply of a liquid which will at least provide the public with a useful choice.

BRIEF SUMMARY OF THE INVENTION

Accordingly in one aspect the invention includes apparatus for measuring the supply of a liquid comprising:
a chamber having a liquid inlet and a liquid outlet, and liquid flow rate detection means to provide a signal indicative of the passing of drops of liquid through a pre-determined cross-section of said chamber, said detection means in turn comprising:
a radiation source, a first concave lens means, which receives radiation from said source, said radiation exiting said first concave lens means in a substantially parallel array of paths, and passing across said chamber, said array of paths constituting said pre-determined cross-section of said chamber, a second concave lens means which receives said radiation from said chamber, said radiation exiting said lens means in a substantially convergent array of paths, and a radiation detector, said convergent array of paths converging on said detector, said detector receiving said radiation and providing a signal which is a function of the intensity of the received radiation, the intensity of said received radiation changing when a drop of liquid passes through said pre-determined cross-section of said chamber.

In a further aspect the invention includes apparatus for measuring the supply status of a liquid comprising:
a chamber having a liquid inlet and a liquid outlet and liquid level detection means to provide a signal if liquid accumulates in the chamber to exceed a pre-determined level, said detection means in turn comprising:
a radiation source, a radiation transmitting medium which receives radiation from said source having a surface which forms part of the interior wall of the chamber at said predetermined level, a portion of said radiation reflecting off said surface,
and a radiation detector receiving from said radiation transmitting medium said reflected radiation and providing a signal which is a function of the intensity of received radiation,
the intensity of said reflected radiation changing when liquid replaces air as the medium in contact with said surface.

In a still further aspect the invention includes apparatus for measuring the supply of liquid comprising:
a chamber having a liquid inlet and a liquid outlet, liquid flow rate detection means to provide a signal indicative of the passing of drops through a pre-determined cross-section of said chamber, said flow rate detection means in turn comprising:
a radiation source, and a radiation detector, which receives radiation from said source that has passed across said chamber at said pre-determined cross-section and provides a signal which is a function of the intensity of the received radiation, the intensity of said radiation changing when a drop of liquid passes through said pre-determined cross-section,
and liquid level detection means to provide a signal if liquid accumulates in the chamber to exceed a pre-determined level.

In a still further aspect the invention includes apparatus for measuring the supply status of a liquid comprising:
a chamber having a liquid inlet and a liquid outlet, a cup positioned in said chamber which receives liquid from said liquid inlet, said cup having an orifice of selected size to provide a calibrated flow of said liquid from said cup, and liquid level detection means to provide a signal if liquid accumulates in said cup to exceed a pre-determined level.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which.

DETAILED DESCRIPTION

Referring to the drawings, a liquid flow control apparatus is shown generally referenced 1. The apparatus 1 is used to supply a liquid such as water preferably in discrete drop form to a humidifying device such as that disclosed in our U.S. Pat. No. 5,062,145 the disclosure of which is incorporated herein by reference. The apparatus 1 is in the form of a chamber 2 which has an inlet 4 and an outlet orifice 58. The inlet 4 generally comprises a non-wicking material, for example, acetal or other non-wicking hydrophobic material in a substantially gas tight arrangement with the upper walls 8 of the chamber. The end of the liquid inlet supply member 10 which is outside the chamber has a conduit 12 attached thereto, the conduit 12 being open to a bag, for example, of liquid such as water which is required to be used to humidify gases which are supplied to a patient such as a patient in a hospital environment. Provided at a selected cross section in the container such as the selected cross section represented by line 14 in FIG. 1, a flow detection radiation transmission means comprising transmitter 16 for example a light emitting diode and a flow detection radiation detection means comprising detector 18 are provided together with radiation transmission means which in the preferred form is formed from, for example, 3-6 mm methyl methacrylate such as perspex transparent sheet member 19 to provide a first part curved surface for example a cylindrical surface transmitting refracting means or lens 21 a first transmitting flat surface which is coated to provide a reflective transmitting surface 23 a second part curved surface transmitting refracting means or lens 20, a first part curved surface receiving lens 22, a first receiving flat surface which is coated to provide a reflective receiving surface 25, a second part curved surface receiving lens 27, which like the lens 21, is formed as a part curved surface of a slot in the member 19 in which slots the transmitter 16, detector 18 are positioned. Radiation transmitter 16 may comprise an infra-red transmitter and the detector means 18 may comprise an infra-red receiver for example. Leases 20 and 22 are used to focus the radiation so that it passes across substantially the whole cross section 14 of the chamber as will be described further below. Preferably radiation in the frequency spectrum in or about the visible spectrum is to be used such as infra-red radiation and the walls of drip chamber 2 are preferably transparent and are of a planar nature and in the cross sectional form of a rectangle to minimise distortion of the radiation passing therethrough. The lenses 20 and 22 and/or the transmitter and detector 16 and 18 may be provided as part of the chamber 2 or may be provided on a separate mounting member so that the chamber 2 may be provided as a "throw away" or disposable article.

Figure 4:
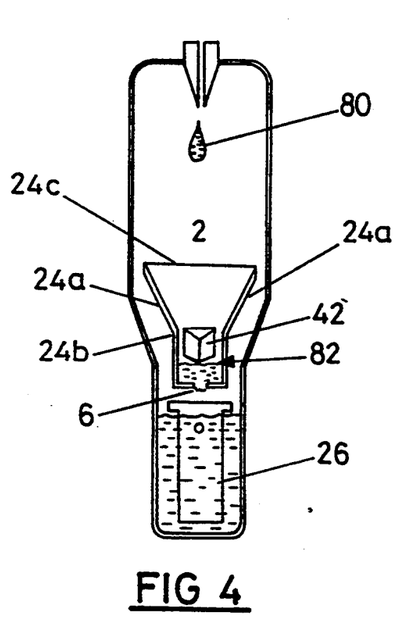
FIGS. 4 and 5 are front elevations in cross-section of a part of the liquid flow control apparatus of FIG. 1.

Interposed between the nozzle 4 and the outlet orifice 58 is a cup 24b shown in FIG. 4, fixed to the walls of the chamber 2 but having openings or spaces 24c as shown in FIG. 4 to permit equalisation of air pressure in the chamber 2. The cup 24b has funnel shaped sides and a prism 42 as part of one other side.

The liquid supply outlet 6 at the base of cup 24b comprises an orifice which is dimensioned so as to allow a calibrated flow of liquid to pass therethrough dependent on the viscosity of the liquid, that is, the outlet 6 provides a "viscosity cup". The overall cross section of the cup 24b reduces in the region 24 and this reduced region provides a measurement area for the volume of liquid in cup 24b. A first moveable valve member 26 is provided for control of the flow of liquid through outlet orifice 58. The valve member 26 pivots about protrusions 28 which are movably retained within a housing 29. The chamber 2 and housing 29 are preferably constructed by moulding, for example, using a plastics material which is transparent in the infrared and in the visible spectrum such as a polystyrene. The valve member 26 could alternatively be provided at the inlet 4 or in the inlet supply line 12.

Figure 1:
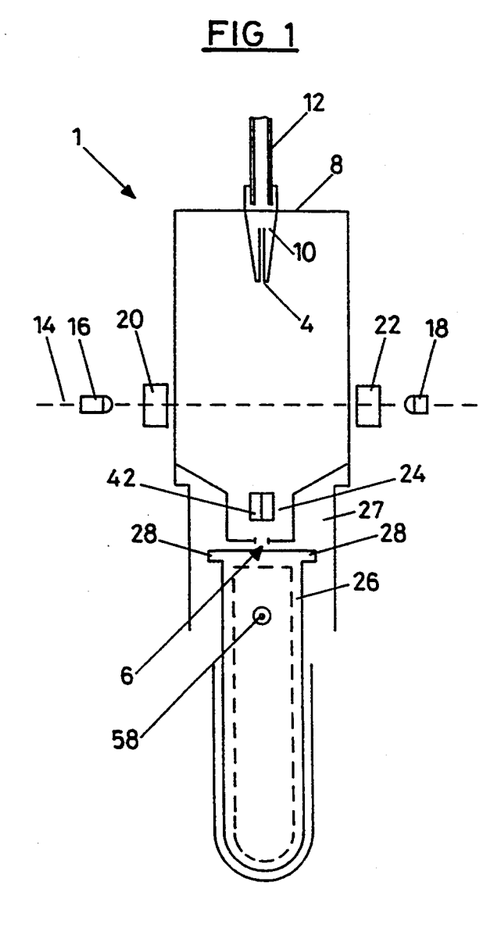
FIG. 1 is a front elevation of a liquid flow control apparatus in accordance with the present invention.
Figure 2:
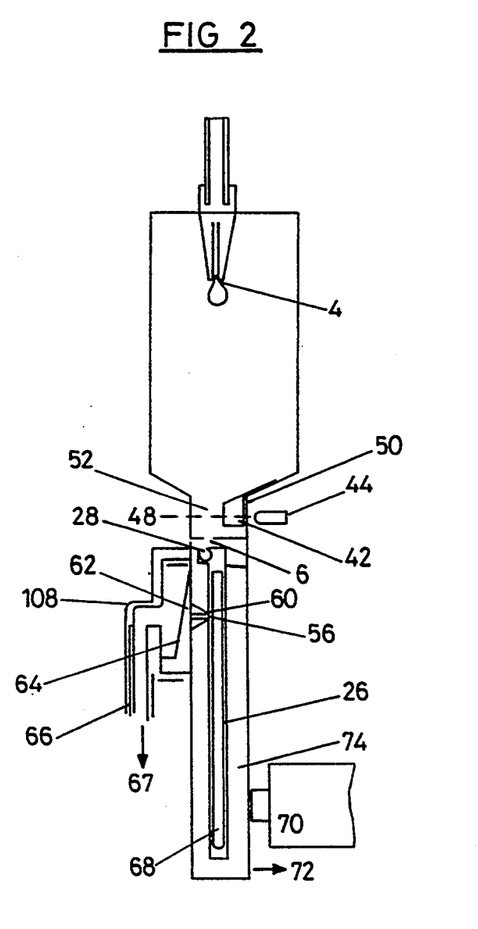
FIG. 2 is a side elevation in cross section of the apparatus shown in FIG. 1.
Figure 3:
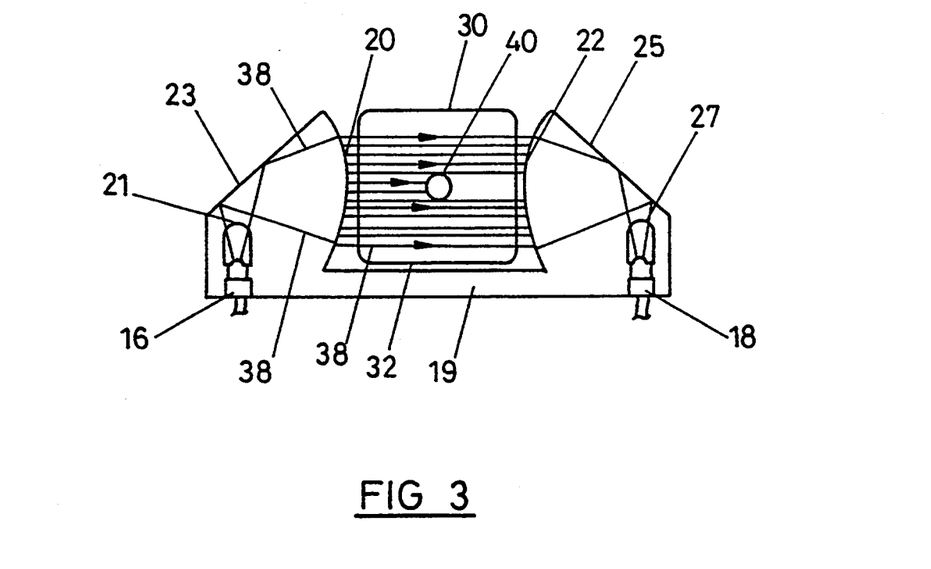
FIG. 3 is a plan view in cross section of the drip chamber of the apparatus shown in FIGS. 1 and 2.

In FIG. 2, a drop of liquid such as water is shown leaving the liquid inlet 4. In practice water will generally be supplied by inlet member 10 in a series of drops. Each drop 40 is detected as it passes across the radiation beam from the transmitter 16 to the detector 18 as is described further below. The indications of drips passing through the chamber which are generated by the detector 18 are passed onto control means (not shown) to control operation of the valve 26 as will be described further below. Referring to FIG. 3, a cross section of the drip chamber such as the cross section indicated by line 14 in FIG. 1 is shown. The sides of the drip chamber are referenced 30, 32, 34 and 36. The transmitter 16 and the detector 18 are mounted so that radiation may pass between opposite sides 34 and 36 of the chamber, but could be turned to allow radiation to pass between sides 30 and 32. Radiation leaving the transmitter 16 is represented by lines 38 in FIG. 3 and it will be seen that the radiation diverges after leaving the transmitter and this divergence is altered by the refractive properties of curved surface forming lens 21 before the radiation is reflected off reflective wall 23 and the divergence is further altered by curved surface forming lens 20 so that the radiation passes across substantially the whole cross section of the chamber and the drop 40 is shown disturbing, impeding or obstructing at least pan of the radiation 38 passing across the chamber. It is desirable that the radiation 38 passes across substantially the whole cross section shown at line 14 (FIG. 1) since the drip chamber 2 may be positioned by a user at an angle so that drops of liquid entering the chamber may fall to one side. If the radiation 38 does not pass across at least the majority of the selected cross section, then some drops may escape detection. After passing through the drip chamber, the radiation is forced to converge upon the receiver 18 by the refractive properties of curved surface of lens 22, reflection off reflective wall 25 and further curved surface of lens 27. The member 19 is a planar member of a moulded plastics material such as an acrylic for example, being approximately 3-6 mm thick and capable of passing radiation, at least in the infrared spectrum. Preferably, all the outer surfaces, except lens surfaces 21, 20, 22 and 27, are coated with a reflective material.

In use, the detector 18 is calibrated to receive a radiation intensity corresponding to that transmitted by the transmitter after passing through lenses 21, 20, 22 and 27 and walls 34 and 36 of the drip chamber when only air is present in the chamber. The presence of a drop such as drop 40 in FIG. 3 will reduce the intensity of the radiation incident on detector 18 and thus reduce the magnitude of the signals supplied by detector 18 to the control means. This reduction in the magnitude of the signal is used by the control means to provide an indication that a drop of liquid has passed into the chamber.

Figure 3A:
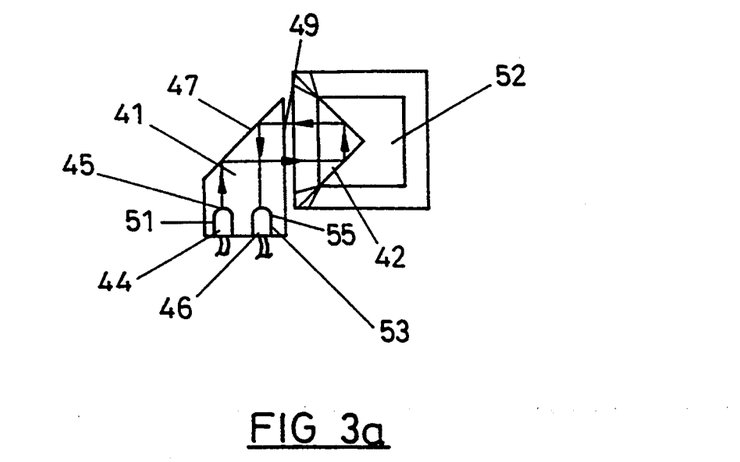
FIG. 3a is a further plan view in cross-section of a lower part of the drip chamber of the apparatus shown in FIGS. 1 and 2.
Figure 7:
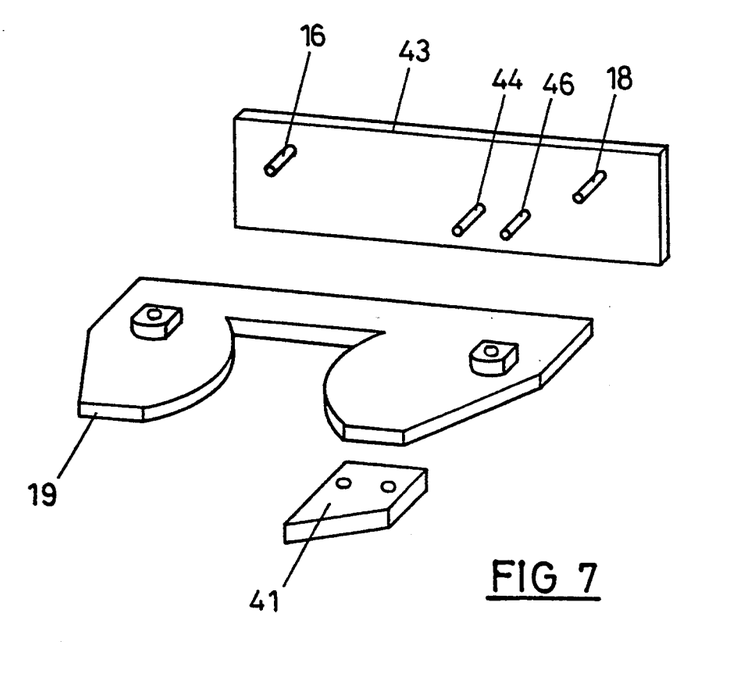
FIG. 7 is an exploded perspective view of a part of the flow control apparatus.

Referring to FIGS. 2 and 3a it will be seen that in region 24 of the drip chamber 2 a prism 42 is provided as part of the wall 50 of the drip chamber. Outside the chamber and adjacent the wall 50 in which the prism 42 is provided, a liquid level radiation transmission means comprising a liquid level detection transmitter 44 such as a light emitting diode emitting radiation in the infrared frequency spectrum, and a liquid level radiation detection means comprising receiver 46 are located beside each other mounted in a lower mounting member 41 at a desired level in the chamber indicated by line 48 in FIG. 2. The mounting member 41 is a moulded plastic member as described above with reference to member 19. The transmitter 44 is mounted in the slot 51 and transmits radiation through a curved lens surface 45 formed on the slot 51, or a flat surface if desired, the radiation reflects off a reflective surface 47 on one edge of member 41 through wall 50 and into the prism 42. The refractive properties of the prism as compared to the refractive properties of air in region 52 adjacent the prism allow internal reflection of the radiation passing through wall 50 into the prism so that the radiation transmitted by the transmitter is received by the receiver 46 which is mounted in a further slot 53 having a curved or flat lens surface 55 beside the transmitter 44 in the same plane indicated by line 48. The external surfaces, excluding surface 49, 45 and 55 of the mounting member 41 are preferably coated with a reflective material to prevent any substantial amount of radiation escaping. The location of infrared transmitters 16 and 44 and detector 18 and receiver 46 on the same side of the chamber allows them to be connected to a single planar printed circuit board. Thus, referring to FIG. 7, the locating member 16 and the mounting member 41 are shown in exploded perspective adjacent to the printed circuit board 43 on which the infrared transmitters and receivers 16, 18, 44 and 46 are mounted. It will be seen that the members 19 and 41 only need to be pressed and secured against the circuit board in the correct position to locate the transmitters and receivers.

The presence of water in region 52, the water being up to the level indicated by line 48 will alter the refractive index in area 52 adjacent the prism so that less radiation transmitted by transmitter 44 will be reflected internally within the prism and less radiation will therefore be incident on receiver 46. The lower level of radiation incident on receiver 46 is provided to the control means (not shown) to provide an indication of the level of liquid in the cup 24b. An indication of the level of liquid in the chamber is important since the drip indicator may fail or water may flow into the chamber in a continuous stream, not discrete drops, and this will rapidly fill the chamber or lead to oversupply of liquid to the point of use. In use the valve member 26 is used to control the flow of liquid through chamber 2. When valve 26 is closed, or when the demand for liquid by the humidifying device is lower than the available rate of delivery of liquid to the chamber 2, liquid is prevented from flowing out of the chamber and the resultant increase of air pressure within the chamber 2 becomes sufficient to prevent further liquid entering the chamber through entry 4.

The cup 24b narrows to a tall narrow column at the base thereof and has sloping sides 24a. At the base of the cup, the orifice or outlet 6 allows liquid to flow therethrough at a predetermined, calibrated rate.

Figure 5:
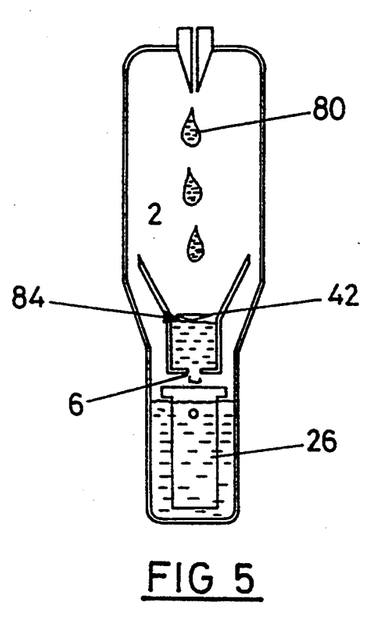

Referring to FIGS. 4 and 5, the outlet 6 is shown in more detail. A further lower chamber area 74 is provided, and liquid flow from this further chamber area is controlled by valve member 26. Liquid flow into lower chamber area 74 (FIG. 2) occurs at a steady flow rate calibrated by the size of orifice 6. As shown in FIG. 4, when droplets 80 of liquid are entering the chamber 2 at an acceptable rate, the level of liquid (represented by arrow 82) in cup 24b is below prism 42. In FIG. 5, when droplets 80 of liquid are entering cup 24b at an undesirably high rate, the level of liquid (represented by arrow 84) in cup 24b is above prism 42 and the liquid surrounds the prism. The change in the level of liquid at the base of cup 24b in the region thereof having a reduced cross section is indicative of the rate of flow of liquid through the apparatus. The relatively small cross sectional area of the lower part of the cup 24b provides greater changes in the level of liquid therein for a given volume of liquid and thus provides greater sensitivity of detection of changes in flow rate. The combination of a calibrated flow outlet and reduced cross sectional area chamber with level detection gives control of the rate of flow of liquid through the apparatus.

Valve member 26 is shown in more detail in FIG. 2. The valve member is biased by pivot supports in the apparatus which contact projections 28 to remain closed. The valve member 26 is resiliently biased against orifice 58 to substantially prevent liquid from flowing therethrough. Orifice 58 has a region 60 there about which provides a first valve seat and a stop for the valve member 26. The other end of a passageway leading to orifice 58 has a region 62 which provides a second valve seat against which a second valve member 64 is resiliently biased. The second valve member 64 is preferably constructed with a resilient material such as a thermoplastic rubber or silicone (TPR). A further outlet 66 is provided through which liquid which has passed through the chamber 2 and the valve means may be passed on to the point of use comprising a humidifying apparatus for example. The direction of flow of liquid to the point of use is indicated by arrow 67.

The valve member 26 also has at least a portion thereof constructed of a magnetically responsive material. In FIG. 2, the valve member 26 is provided as a thermo plastic rubber (TPR) material such as KRATON with an insert 68 of a magnetically responsive material which is responsive to magnetic flux produced by an electromagnet 70. In use, energisation of the electromagnet 70 attracts magnetic insert 68 in valve member 26 toward the electromagnet in a direction shown by arrow 72. Movement in the direction of arrow 72 of the end of the valve member 26 shown provides a sufficient force about the valve member in the location of the spring 56 when pivoting about the fulcrum provided by projections 28 to move the valve member out of contact with the valve seat 60. Such movement allows any water present in chamber 2 to flow through the outlet 6 at a rate determined by the size of the outlet and into further chamber area 74. When chamber area 74 fills up to the level of orifice 58, liquid flows through this orifice. The pressure of the water within chamber area 74 is sufficient to overcome the biasing force which biases valve member 64 against area 62. Thus water will flow through orifice 58 and out further outlet 66. If, however, excessive pressure is present within the humidifying apparatus in connection with outlet 66, for example if pressure is applied to the humidifying envelope described in the aforementioned U.S. Pat. No. 5,062,145, then valve member 64 will be sealably pressed against area 62 so that no substantial volume of liquid flows back into chamber area 74 through orifice 58.

Figure 6:
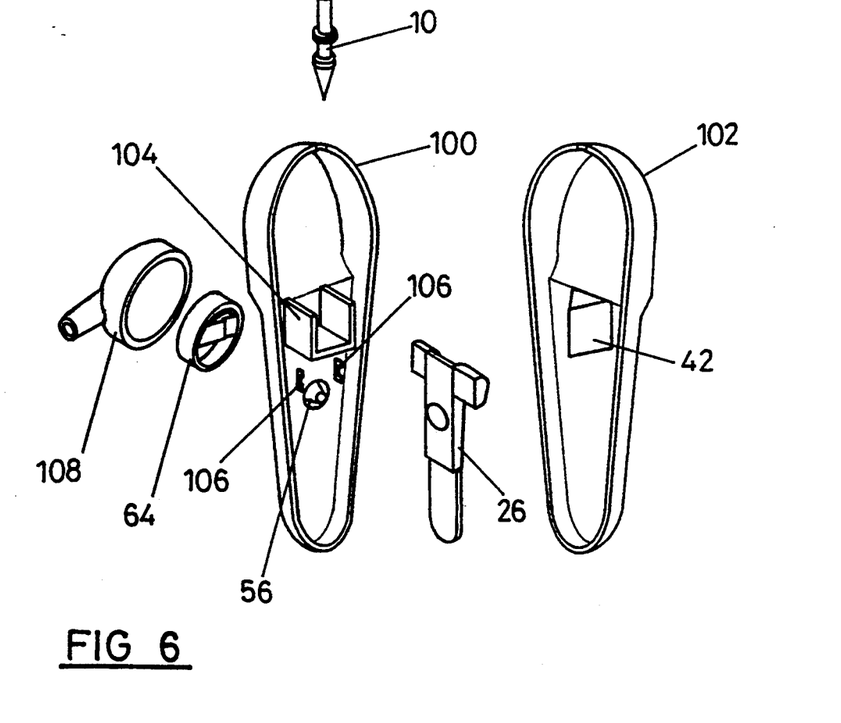
FIG. 6 is an exploded perspective view of the flow control apparatus.

Referring to FIG. 6, the apparatus described above, with the exception of the locating and mounting members 16 and 41 is shown in exploded perspective. It will be seen that the apparatus is constructed from a number of discrete components for easy and cost effective manufacture and assembly. The chamber generally comprises two halves 100 and 102 which are sealably attached to each other by gluing or ultrasonic welding for example. One chamber half 102 includes prism 42, and chamber haft 100 includes walls 104 of cup 24b, and outlet orifice 58. The chamber halves include mounting means 106 for the valve member 26.

The nozzle member 10 is moulded as a single unit as is the non-return valve 64 which is located in outlet tube cap 108.

From the foregoing it will be seen that a method and apparatus is provided for detecting and controlling a flow of liquid for supply to a humidifying device. The apparatus at least in the preferred form provides a number of advantages, some of these being;
   a) The apparatus may be located at an angle and the presence of a level detection means allows further control by providing further information as to the flow of liquid into the drip chamber,
   b) An indication of maximum flow rate of liquid through the apparatus can be detected,
   c) An indication of excess volume of liquid in the chamber is provided,
   d) A relatively small amount of electrical energy is required to operate the device, and
   e) A non return valve is provided to ensure that liquid does not return to the chamber.

I claim:

1. Apparatus for measuring the supply of a liquid comprising:
   a chamber having a liquid inlet and a liquid outlet,
   and liquid flow rate detection means to provide a signal indicative of the passing of drops of liquid through a pre-determined cross-section of said chamber from said liquid inlet, said detection means including a radiating portion mounted on one side of said cross-section and a receiving portion mounted on an opposite side of said cross-section, exteriorly of said chamber:
   said radiating portion including a radiation source, a first concave lens means, which receives radiation from said source, said radiation exiting said first concave lens means in a substantially parallel array of paths, and passing across said chamber, said array of paths constituting said pre-determined cross-section of said chamber, said receiving portion including a second concave lens means which receives said radiation from said chamber, said radiation exiting said lens means in a substantially convergent array of paths, and a radiation detector, said convergent array of paths converging on said detector, said detector receiving said radiation and providing a signal which is a function of the intensity of the received radiation, the intensity of said received radiation changing when a drop of liquid passes through said pre-determined cross-section of said chamber for controlling a fluid condition through the inlet.

2. Apparatus as claimed in claim 1 which includes liquid level detection means to provide a signal if liquid accumulates in the chamber to exceed a pre-determined level.

3. Apparatus as claimed in claim 1 which includes a cup in said chamber which receives liquid from said liquid inlet, said cup having an outlet orifice of selected size to provide a calibrated flow of said liquid therethrough, and liquid level detection means to provide a signal if liquid accumulates in said cup to exceed a pre-determined level.

4. Apparatus as claimed in claim 1 including a first valve member sealingly abutting said liquid outlet, said first valve member moveable to allow liquid flow through said liquid outlet.

5. Apparatus as claimed in claim 4 including a non-return valve external of said liquid outlet which receives liquid from said outlet and prevents said liquid from returning to said outlet.

6. Apparatus as claimed in claim 4 wherein said first valve member is biased by biasing means into a substantially sealed position.

7. Apparatus as claimed in claim 6 wherein said valve member is pivotably supported in said chamber and at lease a portion of said valve member comprises a magnetically responsive material, and said apparatus includes a controllable source of magnetic flux in close proximity to said first valve member.

8. Apparatus for measuring the supply status of a liquid comprising:
   a chamber having a liquid inlet and a liquid outlet
   and liquid level detection means located near the outlet of the chamber to provide a signal if liquid accumulates in the chamber to exceed a predetermined level, said detection means comprising:
   a radiation source, a radiation transmission means which receives radiation from said source and having a surface which forms part of an interior wall of the chamber at said predetermined level, a portion of said radiation reflecting off said surface,
   and a radiation detector receiving from said radiation transmission means said reflected radiation and providing a signal which is a function of the intensity of the received radiation,
   the intensity of said reflected radiation changing when the accumulated liquid rises to replace air and comes into contact with said surface for controlling a measured liquid flow rate through said outlet.

9. Apparatus as claimed in claim 8 including a cup in said chamber, said cup receiving liquid from said liquid inlet, said cup having an outlet orifice of selected size to provide a calibrated flow of said liquid therethrough and said liquid level detection means provide a signal if liquid accumulates in said cup to exceed a pre-determined level.

10. Apparatus as claimed in claim 8 wherein said surface of said radiation transmission means forms a prism protruding into said chamber.

11. Apparatus as claimed in claim 8 including liquid flow rate detection means to provide a signal indicative of the passing of drops through a pre-determined cross-section of said chamber.

12. Apparatus as claimed in claim 11 wherein said liquid flow detection means in turn comprise a second radiation source, at least a portion of the radiation emitted from said source passing across said chamber, and a second radiation detector receiving from said chamber some of said portion of said radiation, and providing a signal which is a function of the intensity of the received radiation, the intensity of said radiation changing when a drop of liquid passes between said second radiation source and said radiation detector.

13. Apparatus as claimed in claim 12 wherein said flow detection means include a first concave lens means, which receives radiation from said source, said radiation exiting said first concave lens means in a substantially parallel array of paths, and passing across said chamber, said array of paths constituting said predetermined cross-section of said chamber, and a second concave lens means which received said radiation from said chamber, said radiation exiting said second concave lens means in a substantially convergent array of paths, said convergent array converging on said second radiation detector, said second radiation detector receiving said radiation, the intensity of said received radiation changing when a drop of liquid passes through said pre-determined cross-section of said chamber.

14. Apparatus as claimed in claim 8 or 11 including a first valve member sealingly abutting said liquid outlet, said first valve member moveable to allow liquid flow through said liquid outlet.

15. Apparatus as claimed in claim 14, including a non-return valve external of said liquid outlet which receives liquid from said outlet and prevents said liquid from returning to said outlet.

16. Apparatus as claimed in claim 14 wherein said first valve member is biased by biasing means into a substantially sealed position.

17. Apparatus as claimed in claim 16 wherein said valve member is pivotably supported in said chamber and at least a portion of said first valve member comprises a magnetically responsive material, and said apparatus includes a controllable source of magnetic flux in close proximity to said first valve member.

18. Apparatus for measuring the supply of liquid comprising:
a chamber having a liquid inlet and a liquid outlet, liquid flow rate detection means to provide a signal indicative of the passing of drops through a pre-determined cross-section of said chamber from said inlet, said flow rate detection means including a radiating portion mounted on one side of said cross-section and a receiving portion mounted on an opposite side of said cross-section exteriorly of said chamber:
said radiating portion including a radiation source, and said receiving portion including a radiation detector, which receives radiation from said source that has passed across said chamber at said pre-determined cross-section and provides a signal which is a function of the intensity of the received radiation, the intensity of said radiation changing when a drop of liquid passes through said pre-determined cross-section,
and liquid level detection means located near the outlet and having a surface which forms part of an interior wall of said chamber at a pre-determined level to provide a signal as the liquid accumulates in the chamber to exceed said pre-determined level that comes into contact with the surface for controlling a measured liquid flow rate through said outlet.

19. Apparatus as claimed in claim 18 including a cup positioned in said chamber which receives liquid from said liquid inlet, said cup having an orifice of selected size to provide a calibrated flow of said liquid therethrough and said liquid level detection means provide a signal if liquid accumulates in said cup to exceed a predetermined level.

20. Apparatus as claimed in claims 18 including a first valve member sealingly abutting said liquid outlet, said first valve member moveable to allow liquid flow through said liquid outlet.

21. Apparatus as claimed in claim 20 including a non-return valve external of said liquid outlet which receives liquid from said outlet and prevents said liquid from returning to said outlet.

22. Apparatus as claimed in claim 20 wherein said first valve member is biased by biasing means into a substantially sealed position.

23. Apparatus as claimed in claim 22 wherein said valve member is pivotably supported in said chamber and at least a portion of said first valve member comprises a magnetically responsive material and said apparatus includes a controllable source of magnetic flux in close proximity to said first valve member.

24. Apparatus for measuring the supply status of a liquid comprising:
a drip chamber having a liquid inlet and a liquid outlet, a cup positioned in said chamber which receives liquid from said liquid inlet, said cup having an orifice of a selected size to provide a calibrated flow of said liquid from said cup, and liquid level detection means located near the outlet in the chamber comprising:
a radiation source, a radiation transmission means which receives radiation from said source and having a surface which forms part of an interior wall of the chamber at a predetermined level, a portion of said radiation reflecting off said surface,
and a radiation detector receiving from said radiation transmission means said reflected radiation and providing a signal which is a function of the intensity of the received radiation,
the intensity of said reflected radiation changing when the accumulated liquid rises to replace air and comes into contact with said surface for controlling a measured liquid flow rate through said outlet.

* * * * *

UNITED STATES PATENT AND TRADEMARK OFFICE
CERTIFICATE OF CORRECTION

PATENT NO. : 5,411,052
DATED : May 2, 1995
INVENTOR(S) : Charles G. Murray

It is certified that error appears in the above-indentified patent and that said Letters Patent is hereby corrected as shown below:

Column 3, Line 55 "leases" should read — lenses —

Column 4, Line 50 "pan" should read —part —

Column 10, Line 21 "claims 18 " should read — claims 18 or 19 —

Signed and Sealed this

Nineteenth Day of September, 1995

*Attest:*

BRUCE LEHMAN

*Attesting Officer*     *Commissioner of Patents and Trademarks*